United States Patent [19]

Frisch et al.

[11] Patent Number: 5,369,082
[45] Date of Patent: Nov. 29, 1994

[54] LIQUID PREPARATION OF HERBICIDE MIXTURES BASED ON GLUFOSINATE

[75] Inventors: Gerhard Frisch, Wehrheim/Taunus; Thomas Maier, Frankfurt am Main, both of Germany

[73] Assignee: Hoechst Aktiengesellschaft, Frankfurt am Main, Germany

[21] Appl. No.: 110,430

[22] Filed: Aug. 23, 1993

Related U.S. Application Data

[62] Division of Ser. No. 822,597, Jan. 17, 1992, Pat. No. 5,238,904.

[30] Foreign Application Priority Data

Jan. 22, 1991 [DE] Germany .............................. 4101691

[51] Int. Cl.$^5$ ...................... A01N 25/30; A01N 43/70; A01N 47/30; A01N 57/04
[52] U.S. Cl. ...................................... 504/127; 504/128; 504/135; 504/148; 71/DIG. 1
[58] Field of Search ................... 504/127, 128

[56] References Cited

U.S. PATENT DOCUMENTS

| | | | |
|---|---|---|---|
| 4,399,287 | 8/1983 | Baillie et al. ...................... | 548/119 |
| 4,400,196 | 8/1983 | Albrecht et al. .................... | 71/86 |
| 4,793,850 | 12/1988 | Koester et al. ..................... | 71/79 |

FOREIGN PATENT DOCUMENTS

| | | |
|---|---|---|
| 0009620 | 4/1980 | European Pat. Off. . |
| 0048436 | 3/1982 | European Pat. Off. . |
| 0297305 | 1/1989 | European Pat. Off. . |
| 0336151 | 10/1989 | European Pat. Off. . |
| 0402769 | 12/1990 | European Pat. Off. . |
| 0402770 | 12/1990 | European Pat. Off. . |
| 0407874 | 1/1991 | European Pat. Off. . |

*Primary Examiner*—Gary E. Hollinden
*Assistant Examiner*—S. Mark Clardy
*Attorney, Agent, or Firm*—Curtis, Morris & Safford

[57] ABSTRACT

The invention relates to comparatively low viscosity aqueous preparations which contain glufosinate and at least one further herbicide active substance dispersed in the aqueous phase, a combination of all α-olefin sulfonate and co-surfactants such as condensation products based on aromatics, alkanols, formaldehyde and disulfite or condensation products based on naphthalenesulfonic acid or ligninsulfonates being employed as surfactants.

19 Claims, No Drawings

LIQUID PREPARATION OF HERBICIDE MIXTURES BASED ON GLUFOSINATE

This application is a division of application Ser. No. 07/822,597, filed Jan. 17, 1992, now U.S. Pat. No. 5,328,9 .

The invention relates to the plant protection agents field, in particular to the formulations of the herbicide glufosinate (i.e. 2-amino-4-(hydroxymethylphosphinyl)-butanoic acid and its salts, also known as phosphinothricin, see U.S. Pat. No. 4,168,963) and its salts in combination with at least one herbicide dispersed in the aqueous phase.

Aqueous formulations of the active compound glufosinate have been disclosed (see EP-A-48436 or U.S. Pat. No. 4,400,196), and also combinations of glufosinate with various active compounds based on substituted phenylurea derivatives such as linuron (see EP-A-0402769) or monolinuron (see EP-A-0402770) and with triazines such as, for example, simazine with diuron (see EP-A-0297305). These formulations are in some cases on the market and are satisfactory in terms of use. However, they are in some cases of comparatively high viscosity. This is frequently a peculiarity of combination formulations; since it is usually necessary with these to employ a particular mixture of surfactants in order to be able to prepare formulations which are stable on storage and satisfactory in terms of use, the content of surfactant is rather higher than in formulations of an individual active compound.

It is known to the person skilled in the art that an immensely large number of properties of the components in two- or multi-phase systems can have influence on the stability of these systems. Owing to the variable ionicity of the particular solution, the surface charge and nature of the particles, their solubility, the degree of coating and the type of coating of the dispersed particles by the appropriate surfactants including their steric, entropic and electrostatic properties alone—to mention some effects which play a decisive role in the stability over time of a two- or multi-phase system—it is hardly successful when drawing up recipes for the preparation of novel formulations only to think in terms of analogies. In many cases, relatively high-percentage dispersion formulations can be prepared, for example, using a certain surfactant combination, as is the case in some of the abovementioned examples. With the same surfactant composition, however, if the active substance content is changed, for example, to smaller values, then in a very large fraction of the cases the system becomes unstable, i.e. separation, sedimentation, cementation etc. occur even after a short residence time. In the field of pesticide formulation it is therefore not to be expected that surfactants a, b and c will be useful and suitable for a formulation containing x and y as the active ingredients if such surfactants are already known for a formulation containing y and z as the active ingredients. This is especially true if the surfactants of the known formulation are not equivalent to a, b and c.

The same is also true in a multi-phase system for the viscosity of the system. With the same active substance composition, the viscosity is determined not only by the fineness of the dispersed particles, but also particularly strongly by the type of surfactant in the system. In systems containing dispersed particles, a higher viscosity is of advantage to minimize the sedimentation of the particles. If, however, the viscosity is too high, problems result, in particular when emptying containers and when preparing the spray liquor.

It is also known that the viscosity of aqueous solutions which contain lauryl ether sulfate sodium salts depends sensitively on the electrolyte content of the solution. For example, the viscosity in a mixture of 15% Na lauryl ether sulfate, 1% NaCl and 84% water at 20° C. is of the order of 23 mPas, but 74,000 mPas with an addition of 6% NaCl (mPas=millipascal second, measured with a Höppler viscometer, values from ®Genapol LRO paste data sheet, Hoechst AG, 1982).

According to EP-A-0048436 (U.S. Pat. No. 303,373), Na lauryl ether sulfates are particularly suitable auxiliaries to display the action of glufosinate particularly well. Na lauryl ether sulfate is also mentioned as a constituent of the formulations in EP-A-0297305; in this case, comparatively very high viscosity values are found (for example about 3200 mPas at 13 rpm and about 1770 mPas at 112 rpm, measured at about 20° using the Rheomat 115 rotary viscometer from Contraves), which can lead to problems during preparation and use. In particular, on account of the salt of glufosinate customarily employed and the strong dependence of the viscosity on the salt content, the active compound content in formulations of this type must be kept comparatively low.

The object is therefore to provide stable aqueous mixed formulations containing glufosinate, which are of comparatively low viscosity and enable a comparable to better display of action of the active substances without containing lauryl ether sulfate compared with the formulations which contain lauryl ether sulfate as the principal surfactant.

The invention relates to aqueous herbicide preparations which contain glufosinate or its salts in dissolved form and at least one further herbicide active substance in dispersed form, which preparations contain a) 0.1 to 60% by weight, preferably 2 to 45% by weight, of an active substance combination of
   a1) glufosinate or its salts and at least
   a2) one dispersed herbicide active substance, preferably dispersed in solid form (suspended) in the ratio 1:100 to 100:1, preferably 1:10 to 10:1, in particular 1:5 to 3:1, of the active substances a1:a2, b) 0.5 to 30% by weight, relative to active substance, preferably 1.5 to 24% by weight, of a surfactant from the long-chain α-olefin sulfonate group, c) 0.5 to 20% by weight, relative to active substance, preferably 1 to 10% by weight, of one or more co-surfactants from the group comprising condensation products based on aromatics (for example cresols, phenols), alkanals and disulfite, condensation products based on naphthalenesulfonic acids or their salts and ligninsulfonates, d) 10 to 70% by weight, preferably 15 to 55% by weight, of water and e) 0 to 15% by weight, preferably 5 to 10% by weight, of customary auxiliaries, such as thickeners, antifoam agents, preservatives, antifreezes and agents preventing drying up.

The aqueous herbicidal active substance formulations according to the invention based on glufosinate contain at least 2 phases, i.e. the aqueous phase in which glufosinate is dissolved, and at least one further liquid or solid phase which contains one or more herbicide active substances and is dispersed in the aqueous phase.

Preferably, suitable active substances of the type a2 are those which are present in the preparation according to the invention in solid dispersed form. Examples which are suitable are phenylurea derivatives, such as, for example, diuron, linuron, monolinuron, isoproturon, chlortoluron, neburon and monuron, and/or triazines, such as, for example, simazine, atrazine and terbuthylazine. Said herbicides are generally known and are described, for example, in "The Pesticide Manual" 9th edition, British Crop Protection Council 1991. Diuron and/or simazine are preferred.

As a rule, 0.1–30% by weight, preferably 2–22% by weight, of glufosinate or its salts and as a rule 0.1–45% by weight, preferably 2–37% by weight, of the solid suspended active substance(s) are contained in the mixture. If available, both the optically pure isomers of the active substances and their mixtures can be employed.

The surfactant mixture employed according to the invention is composed of at least two components which surprisingly allow preparations having an active substance content of 60% by weight to be prepared, which are of low viscosity, stable on storage and satisfactory in use.

The surfactants (b) are preferably long-chain olefin sulfonates having 12 to 20 carbon atoms, in particular a $C_{12}$–$C_{20}$-α-olefin sulfonate sodium salt having a substantial content of $C_{14}$–$C_{16}$ (®Hostapur OSB, Hoechst AG), which can be present, for example, either in powder form or in aqueous solution.

Suitable co-surfactants are: condensation products based on aromatics (cresols, phenols) with formaldehyde and disulfite, such as, for example, Hoe S1494 (condensation product based on cresol, alkylphenol, formaldehyde and sodium disulfite; Hoechst AG), in aqueous solution or as a powder, and ®Tamol NN 8906 (Na salts of naphthalenesulfonic acid condensation products, BASF), or alternatively ligninsulfonates, such as, for example, ®Borresperse 3A, ®Vanisperse CNH (Borregard Sarpsborg/Norway). The ratio of the co-surfactant to the α-olefin sulfonate is preferably from 1:20 to 10:1, in particular 1:15 to 5:1.

The preparation according to the invention can additionally contain customary formulation auxiliaries such as commercially available thickeners, for example those based on polysaccharides such as ®Rhodopol 23 (Rhone Poulenc) or ®Kelzan 5 (Kelco Corp., USA), those based on methylcellulose such as the ®Tylose series from Hoechst, compositions based on inorganic compounds such as the ®Darvan series (Vanderbilt Corp., USA) or ®Bentone series (NL Chemicals), antifoams based on silicone such as the antifoam emulsions or compositions series from Wacker or the ®Silcolapse or ®Rhodorsil series from Rhone Poulenc, antifreezes and/or compositions preventing drying up based on polyols, such as ethylene glycols, propylene glycol, glycerol and polyalkylene glycols, and urea. The formulations can also contain commercially available preservatives.

The preparations according to the invention can be prepared in the customary manner by wet grinding of the total combination of active substances and auxiliaries or of the solid fraction with water and auxiliaries. The preparations can also be prepared, for example, by the process described in EP-A-0130370, in which an aqueous active substance dispersion of the active substance or substances of the type a2) according to the invention is metered into a colloid mill together with an aqueous solution of glufosinate or its salt and intimately mixed.

Examples of the preparations according to the invention are listed in Tables 1 and 2 below.

The viscosity of the preparations according to the invention is surprisingly low or makes possible, with the same viscosity, higher active substance contents than comparable formulations containing Na lauryl ether sulfate as the principal surfactant. For example, in Examples 1 and 2 of Table 1 about 250 mPas was measured as the viscosity at 20° C. and 13 rpm of the viscometer (Rheomat 115, Contraves) and about 100 mPas at 112 rpm. Comparatively low viscosities are obtained in the other examples.

The biological activity which is obtained when using the preparations according to the invention in comparison with tank mixes of glufosinate containing Na lauryl ether sulfate as a commercial formulation and an aqueous dispersion of diuron at an equal application rate of active substance is equally good to sometimes better.

TABLE 1

|  | 1 | 2 | 3 | 4 | 5 | 6 | 7 | 8 | 9 | 10 | 11 | 12 | 13 |
|---|---|---|---|---|---|---|---|---|---|---|---|---|---|
| Glufosinate | 10.7 | 10.7 | 7 | 7 | 7 | 8.5 | 7 | 7 | 7 | 7 | 7 | 11.4 | 9.7 |
| Diuron | 16.0 | 16.0 | 28 | 28 | 16.5 | 28 | 28 | 28 | 28 | 28 | 28 | 21.8 | 18.7 |
| Simazine |  |  |  |  |  | 10.9 |  |  |  |  |  | 14.5 | 12.5 |
| Hostapur OSB | 9.9 | 9.9 | 9.9 | 9.9 | 9.9 | 9.9 | 9.9 | 9.9 | 9.9 | 9.9 | 9.9 | 9.9 | 9.9 |
| Tamol NN 8906 |  |  |  | 2.0 | 2.0 |  |  |  |  | 1.0 |  | 2 | 2 |
| Vanisperse CNH |  |  |  |  |  |  |  |  |  |  | 4.0 |  |  |
| Borresperse 3A |  | 2.0 |  | 1.0 |  |  |  |  |  |  |  |  |  |
| Hoe S1494 | 6.0 |  | 6.0 | 2.0 |  | 6.0 | 3.0 | 4.0 | 5.0 | 6.0 |  | 6 | 6 |
| Antifoam agent | 2.0 | 2.0 | 3.0 | 3.0 | 2.0 | 2.0 | 2.0 | 2.0 | 2.0 | 2.0 | 2.0 | 2 | 2 |
| Bentone EW | 0.1 | 0.1 | 0.1 | 0.1 | 0.1 | 0.1 | 0.1 | 0.1 | 0.1 | 0.1 | 0.1 | 0.10 | 0.1 |
| Darvan No. 1 | 1.0 |  |  | 1.0 |  |  |  |  |  |  |  |  |  |
| Darvan No. 3 |  | 1.0 | 1.0 |  |  | 0.4 | 1.0 | 1.0 | 0.5 |  | 1.0 | 0.4 |  |
| Genapol X-080 |  |  |  |  | 0.3 |  |  |  |  |  |  | 0.3 |  |
| Propylene glycol | 6.0 | 6.0 | 6.0 | 6.0 | 6.0 | 4.0 | 6.0 | 6.0 | 6.0 | 6.0 | 6.0 | 4 | 4 |
| Water | 49.3 | 52.3 | 39 | 39 | 55.5 | 29.9 | 43 | 42 | 41.5 | 40 | 42 | 27.6 | 35.1 |

TABLE 2

|  | 14 | 15 | 16 | 17 | 18 | 19 | 20 | 21 | 22 | 23 | 24 | 25 | 26 |
|---|---|---|---|---|---|---|---|---|---|---|---|---|---|
| Glufosinate | 7 | 6 | 5.5 | 9.5 | 22 | 13 | 13 | 13 | 10.3 | 10.3 | 10.3 | 10.3 | 10.3 |
| Diuron | 28 | 24 | 8 | 18.5 | 9 |  |  |  |  |  |  |  |  |
| Simazine |  |  |  |  |  | 32.5 | 33 | 32.5 | 26.5 | 26.5 | 26.5 | 26.5 | 26.5 |
| Hostapur OSB | 10 | 8 | 22 | 2 | 10 | 9.9 | 10 | 10 | 9.9 | 10 | 10 | 10 | 10 |
| Tamol NN 8906 |  |  |  |  |  |  |  |  |  |  |  |  |  |
| Vanisperse CNH |  |  |  |  |  |  |  |  |  |  |  |  |  |
| Borresperse 3A |  |  |  |  |  |  |  |  |  |  |  | 2 | 2 |

TABLE 2-continued

|  | | | | | | | | | | | | | |
|---|---|---|---|---|---|---|---|---|---|---|---|---|---|
| Hoe S1494 | 1 | 10 | 2 | 6 | 3 | 6 | 6 | 6 | 6 | | | 6 | 6 |
| Antifoam agent | 2 | 2 | 3 | 2 | 2 | 2 | 2 | 2 | 2 | 2 | 2 | 2 | 3 |
| Darvan No. 1 | | | | | | | | | | | | | |
| Darvan No. 3 | 0.5 | 0.5 | 1 | 1 | 1.0 | | 1.0 | 0.4 | 1.0 | | 1.0 | 1.0 | |
| Genapol X-080 | | | | | | 1 | | 0.3 | 1.0 | 1.0 | 1.0 | 1.0 | 1.0 |
| Propylene glycol | 6 | 6 | 6 | 6 | 6 | 6 | 6 | 6 | 6 | 6 | 6 | 6 | 6 |
| Genapol PF40 | | | | | | | | | | | | | |
| Benetone EW | 0.1 | 0.2 | 0.4 | 0.1 | 0.2 | 0.1 | 0.1 | 0.1 | 0.1 | 0.1 | 0.1 | 0.1 | 0.1 |
| Water | 45.4 | 43.3 | 52.1 | 54.9 | 46.8 | 29.5 | 28.9 | 29.5 | 37.2 | 39.1 | 43.1 | 37.1 | 37.1 |

|  | 27 | 28 | 29 | 30 | 31 | 32 | 33 | 34 |
|---|---|---|---|---|---|---|---|---|
| Glufosinate | 5 | 10.3 | 10.3 | 13.3 | 7 | 9.5 | 12.5 | 20 |
| Diuron | | | | | | | | 8 |
| Simazine | 13 | 26.5 | 26.5 | 32.5 | 17.5 | 24 | 32 | |
| Hostapur OSB | 24 | 10 | 9.9 | 10 | 9.6 | 10 | 11 | 10 |
| Tamol NN 8906 | | 2 | 2 | | | | | |
| Vanisperse CNH | | | | | | | | 4.0 |
| Borresperse 3A | 2 | 2 | 2 | 2 | | | 2 | 2 |
| Hoe S1494 | | | | | 6 | 6 | | |
| Antifoam agent | 3 | 3 | 3 | 3 | 3 | 3 | 3 | 2 |
| Darvan No. 1 | | | 1.0 | | | | | |
| Darvan No. 3 | 1.0 | | | 1.0 | 1.0 | 1.0 | 1.0 | 1.0 |
| Genapol X-080 | 1.0 | | | 1.0 | 1.0 | 1.0 | 1.0 | 1.0 |
| Propylene glycol | 6.0 | 6.0 | 4.0 | 4.0 | 6 | 6 | 6 | 6 |
| Genapol PF40 | | 1.0 | | | | | | |
| Bentone EW | 0.3 | 0.1 | 0.1 | 0.05 | 0.1 | 0.1 | 0.1 | 0.2 |
| Water | 44.7 | 39.1 | 41.2 | 33.15 | 48.8 | 39.4 | 31.4 | 49.8 |

Abbreviations in Tables 1 and 2
Glufosinate = glufosinate ammonium salt
Hostapur OSB = Na α-olefin sulfonate containing substantial $C_{14}$–$C_{16}$ (Hoechst)
Tamol NN 8906 = Na salt of a naphthalenesulfonic acid condensation product (BASF)
Vanisperse CNH = ligninsulfonate (Borregard)
Borresperse 3A = ligninsulfonate (Borregard)
Hoe S1494 = condensation product based on cresol, alkylphenol, formaldehyde and sodium bisulfite (Hoechst)
Bentone EW = thickener based on magnesium montmorrilonite (NL Chemie)
Darvan No. 1 = sodium salt of polymerized alkylnaphthalenesulfonic acids (Vanderbilt Corp.)
Darvan No. 3 = sodium salt of polymerized substituted alkylbenzenesulfonic acids, contains inorganic suspending agent (Vanderbilt Corp.)
Genapol X080 = fatty alcohol polyglycol ether (Hoechest)
Genapol PF40 = block polymer of ethylene oxide and propylene oxide (Hoechest)

We claim:

1. A herbicidal aqueous preparation which contains glufosinate or its salts in dissolved form and at least one further herbicide active substance in dispersed form, said preparation consisting essentially of:
   a) 0.1 to 60% by weight of an active substance combination of
      a1) glufosinate or its salts and at least
      a2) one dispersed herbicide active substance selected from the group consisting of linuron, monolinuron, isoproturon, chlortoluron, neburon, monuron, simazine, atrazine and terbuthylazine in the ratio 1:100 to 100:1 of the active substances a1:a2,
   b) 0.5 to 30% by weight, relative to active substance, of a surfactant from the long-chain α-olefin sulfonate group,
   c) 0.5 to 20% by weight, relative to active substance, of one or more co-surfactants selected from the group consisting of condensation products based on aromatics, alkanols and disulfites, condensation products based on naphthalenesulfonic acids or their salts and ligninsulfonates,
   d) 10 to 70% by weight of water and
   e) 0 to 15% by weight of customary auxiliary.

2. A preparation as claimed in claim 1, which contains
   a) 2 to 45% by weight of an active substance combination of
      a1) glufosinate or its salts and at least
      a2) one dispersed herbicide active substance in the ratio 1:10 to 10:1 of the active substances a1:a2,
   b) 1.5 to 24% by weight, relative to active substance, of a surfactant from the long-chain α-olefin sulfonate group,
   c) 1 to 10% by weight, relative to active substance, of co-surfactants,
   d) 15 to 50% by weight of water and
   e) 5 to 10% by weight of customary auxiliary.

3. A preparation as claimed in claim 1, which contains simazine as active substance a2.

4. A preparation as claimed in claim 1, wherein glufosinate ammonium salt is employed as the active substance of the type a1.

5. A preparation as claimed in claim 1, wherein a $C_{12}$–$C_{20}$-α-olefin sulfonate sodium salt having a substantial content of $C_{14}$–$C_{16}$ is employed as component b).

6. A process for controlling undesired plant growth, which comprises applying an effective amount of one of the preparations defined in claim 1 to the plants and/or their cultivation area.

7. A herbicidal aqueous preparation which has a viscosity of about 250 mPas at 20° C. and 13 rpm and about 100 mPas at 112 rpm and contains glufosinate or its salts in dissolved form and at least one further herbicide active substance in dispersed form, which preparation comprises
   a) 0.1 to 60% by weight of an active substance combination of
      a1) glufosinate or its salts and at least
      a2) one dispersed herbicide active substance selected from the group consisting of linuron, monolinuron, isoproturon, chlortoluron, neburon, monuron, simazine, atrazine and terbuthylazine in the ratio 1:100 to 100:1 of the active substances a1:a2,
   b) 0.5 to 30% by weight, relative to active substance, of a surfactant from the long-chain α-olefin sulfonate group, c) 0.5 to 20% by weight, relative to active substance, of one or more co-surfactants selected from the group consisting of condensation products based on aromatics, alkanols and disulfites, condensation products based on naphthalenesulfonic acids or their salts and ligninsulfonates, d) 10 to 70% by weight of water and e) 0 to 15% by weight of customary auxiliary.

8. A preparation as claimed in claim 7, which contains a) 2 to 45% by weight of an active substance combination of a1) glufosinate or its salts and at least a2) one dispersed herbicide active substance selected from the group consisting of linuron, monolinuron, isoproturon, chlortoluron, neburon, monuron, simazine, atrazine and terbuthylazine in the ratio 1:10 to 10:1 of the active substances a1:a2, b) 1.5 to 24% by weight, relative to active substance, of a surfactant from the long-chain α-olefin sulfonate group, c) 1 to 10% by weight, relative to active substance, of co-surfactants, d) 15 to 50% by weight of water and e) 5 to 10% by weight of customary auxiliary.

9. A preparation as claimed in claim 7, which contains simazine as active substance a2.

10. A preparation as claimed in claim 7, wherein glufosinate ammonium salt is employed as the active substance of the type a1.

11. A preparation as claimed in claim 7, wherein a $C_{12}$–$C_{20}$-α-olefin sulfonate sodium salt having a substantial content of $C_{14}$–$C_{16}$ is employed as component b.

12. A process for controlling undesired plant growth, which comprises applying an effective amount of one of the preparations defined in claim 7 to the plants and/or their cultivation area.

13. A herbicidal aqueous preparation which contains glufosinate or its salts in dissolved form and at least one further herbicide active substance in dispersed form, said preparation consisting of:

a) 0.1 to 60% by weight of an active substance combination of a1) glufosinate or its salts and at least a2) one dispersed herbicide active substance selected from the group consisting of linuron, monolinuron, isoproturon, chlortoluron, neburon, monuron, simazine, atrazine and terbuthylazine in the ratio 1:100 to 100:1 of the active substances a1:a2, b) 0.5 to 30% by weight, relative to active substance, of a surfactant from the long-chain α-olefin sulfonate group, c) 0.5 to 20% by weight, relative to active substance, of one or more co-surfactants selected from the group consisting of condensation products based on aromatics, alkanols and disulfites, condensation products based on naphthalenesulfonic acids or their salts and ligninsulfonates, d) 10 to 70% by weight of water and e) 0 to 15% by weight of customary auxiliary.

14. A preparation as claimed in claim 13, which contains a) 2 to 45% by weight of an active substance combination of a1) glufosinate or its salts and at least a2) one dispersed herbicide active substance selected from the group consisting of linuron, monolinuron, isoproturon, chlortoluron, neburon, monuron, simazine, atrazine and terbuthylazine in the ratio 1:10 to 10:1 of the active substances a1:a2, b) 1.5 to 24% by weight, relative to active substance, of a surfactant from the long-chain α-olefin sulfonate group, c) 1 to 10% by weight, relative to active substance, of co-surfactants, d) 15 to 50% by weight of water and e) 5 to 10% by weight of customary auxiliary.

15. A preparation as claimed in claim 13, which contains simazine as active substance a2.

16. A preparation as claimed in claim 13, wherein glufosinate ammonium salt is employed as the active substance of the type a1.

17. A preparation as claimed in claim 13, wherein a $C_{12}$–$C_{20}$-α-olefin sulfonate sodium salt having a substantial content of $C_{14}$–$C_{16}$ is employed as component b).

18. A process for controlling undesired plant growth, which comprises applying an effective amount of one of the preparations defined in claim 13 to the plants and/or their cultivation area.

19. A process for the production of the preparation defined in the claim, 7 having a viscosity of about 250 mPas at 20° C. and 13 rpm and about 100 mPas at 112 rpm, said process comprising finely mixing the components a) to e) and finely grinding in a dispersing or colloid mill.

* * * * *